| United States Patent [19] | [11] Patent Number: 4,804,651 |
| Duvic et al. | [45] Date of Patent: Feb. 14, 1989 |

[54] METHODS AND COMPOSITIONS FOR THE TREATMENT OF PSORIASIS

[75] Inventors: Madeleine Duvic; Gary W. Brewton, both of Houston, Tex.

[73] Assignee: Board of Regents, The University of Texas System, Austin, Tex.

[21] Appl. No.: 59,907

[22] Filed: Jun. 9, 1987

[51] Int. Cl.$^4$ ............................................. A61K 31/70
[52] U.S. Cl. ..................................... 514/50; 514/863; 514/934
[58] Field of Search ........................... 514/50, 863, 934

[56] References Cited

PUBLICATIONS

Christophers et al. (1986), "Psoriasis", Chapter 42 of *Dermatology in Medicine*, 3rd Edition, Fitzpatrick et al., eds., pp. 461–491.
Summary Report, Retrovir (Zidovudine), (1987), Investigators/Clinicians Forum Held Dec. 20, 1987.
The Retrovir (Zidovudine) distribution program (1987).
Retrovir (Zidovudine), From Discovery to Patient, date unknown.
Ruzicka et al. (1987), *The Lancet*, Dec. 19, 1987, pp. 1469–1470.
Burrough's Wellcome protocol—"Uncontrolled Clinical Trial of the Long Term Safety of AZT".
NIAID Backgrounder, "ATEU Investigators Plan AZT Studies" Sep., 1986.
NCI Cancer Facts, "Azidothymidine Research at NCI" Sep., 1986.
Anderson et al., "*Psoriasis in Pathogenesis of Skin Disease*", pp. 67–84.

*Primary Examiner*—Leonard Schenkman
*Attorney, Agent, or Firm*—Arnold, White & Durkee

[57] ABSTRACT

Disclosed are methods and compositions employing azidothymidine for the treatment of psoriasis. Oral, parenteral or topical dosage forms are administered to affected individuals in therapeutically effective amounts. Typically, between about 100 and about 4000 mg of azidothymidine is administered orally per day until symptoms of the disease such as inflammation, irritation, or incidence or size of lesions, are abated. Also disclosed are topical dosage forms, including pharmaceutically acceptable creams, lotions, ointments, salves and the like, which include therapeutically effective concentrations of azidothymidine. Such topical compositions may further include effective amounts of a corticosteroid or a cutaneous surface acting antipsoriatic agent, such as a keratolytic agent.

21 Claims, No Drawings

METHODS AND COMPOSITIONS FOR THE TREATMENT OF PSORIASIS

BACKGROUND OF THE INVENTION

1. Field of the Invention

The present invention relates to compositions employing 3'-azido-3'-deoxythymidine (hereinafter azidothymidine or AZT) and their use in the treatment of psoriasis.

2. Description of the Related Art

Psoriasis is a common skin disorder characterized by epidermal proliferation and dermal inflammation. The disease may present a number of clinical manifestations, generally related to the severity or stage of the outbreak. Clinically, patients afflicted with psoriasis exhibit symptoms ranging from mild localized inflammation or irritation to severe pruritic lesions. Moreover, acute manifestations of the disease can lead to additional severe problems such as psoriatic arthritis and exfoliative erythroderma.

Although first recognized more than two centuries ago, and afflicting about 2 persons in every 100, the pathogenesis of psoriasis remains speculative. Although many theories have been put forth, the clinical diversity of the disease along with a lack of good animal models have made a definitive characterization of the disease elusive. Recent research has suggested a complex etiology possibly involving the interaction of intrinsic cellular defects and environmental factors (see, e.g., Anderson et al. (1986), "Psoriasis," Chapter 7 in *Pathogenesis of Skin Disease*, eds. Thiers and Dobson, pp. 67–85). Some evidence suggests the disease is a heritable disorder, or perhaps secondary to a vertically transmitted retrovirus.

By studying defects characterized in epidermal and related cells, a proposed cascade of pathogenic events which attempts to account for most of the observations have been summarized by Anderson et al., supra. Defective cell membrane function and cyclic nucleotide regulation may in turn result in altered polyamine, proteinase or arachidonic acid transformations. These changes may cause the epidermis to be primed to be hyperproliferative and the dermal microvasculative to overrespond to injury. Once the psoriatic process is triggered, inflammatory mediators and the immune system may produce a "positive feedback" exacerbation until treatment or negative regulatory factors supervene. Genetic, retroviral and environmental influences may work at all these levels.

Unfortunately, psoriasis treatment protocols and agents have generally proved inadequate, particularly in the treatment of more serious forms of the disease. Antiinflammatory steroids have been used extensively in the treatment of all forms of psoriasis. For milder forms of the disease, topical steroid preparations and various surface-acting type agents such as mild irritants or antiseptics which may or may not have keratolytic properties, have been used. Examples of drugs employed as cutaneous surface-acting drugs in the treatment of psoriasis include substituted phenols such as cresol, tars, coal tars, miscellaneous topical germicides such as sulfur, ichthammol and anthralin.

For severe chronic or acute psoriasis, systematic administration of various antimetabolites and corticosteroids has generally been the treatment of choice. For example, methotrexate, a folic acid antagonist, is often employed in the treatment of more severe forms such as exfoliative psoriasis, generally in dose ranges of about 2.5 to 5.0 mg orally for five days, or 25 to 50 mg intravenously weekly. However, dose levels necessitated by a very severe case can lead to leukopenia and other potentially life threatening toxicities.

Other types of antimetabolites often employed in the treatment of psoriasis include both purine and pyrimidine analogs. For example, azaribine (triazure), a triacetyl derivative of azauridine, has been effective in the treatment of generalized psoriasis and polycythemia vera. It has been suggested that azaribine acts through the inhibition of pyrimidine biosynthesis in affected cells. Purine analogs such as azathioprine have also been employed in treating psoriasis. This drug may act through an immunomodulation mechanism in that it has also been employed to suppress the immune response, for example, in the prevention of the rejection phenomena in organ transplantation.

Existing protocols for the treatment of other autoimmune diseases such as vitiligo and lupus erythematosus has similarly been lacking, due in large part to the lack of knowledge concerning the etiology of such diseases. In general, many of the agents used in treating psoriasis have also been used in the treatment of other autoimmune diseases such as lupus. These include, for example, the above-mentioned cutaneous surface acting agents as well as corticosteroids, both topical and systemic. In vitiligo, agents such as methoxsalen and trioxalen are also employed to increase skin tolerance to sunlight and to facilitate repigmentation of the skin. Although the foregoing agents have found some use in the treatment of autoimmune disease, they clearly do not represent ideal treatment modalities.

Unfortunately, there has been up until now no clear drug of choice in the treatment of autoimmune disease, and particularly, for the treatment of severe exfoliative processes or highly pruritic lesions such as are seen in psoriasis. Without a clear understanding of the disease pathology, or a common structure-activity relationship separating useful from marginally or unuseful agents, specific drug design for anti-psoriatic agents has been thwarted. There is accordingly an urgent need to identify pharmaceutical agents useful in the treatment of psoriasis, and particular agents active in the more severe forms.

SUMMARY OF THE INVENTION

It is therefore an object of the present invention to provide a method of treating psoriasis, which addresses at least some of the disadvantages present in the prior art.

It is an additional object of the present invention to provide a treatment method that is particularly applicable to the treatment of more severe forms of psoriasis.

It is still a further object of the invention to provide a treatment method which may be administered by virtually any common route of administration, including but not limited to oral, parenteral and topical routes.

Accordingly, in its most general and overall scope, the present invention is directed to the treatment of psoriasis in an individual comprising administering to the individual an amount of azidothymidine that is effective to reduce the inflammation, irritation, or incidence or size of lesions, associated with this disease.

In certain embodiments, the treatment method may be characterized as comprising the steps of: (a) diagnosing an individual as having psoriasis; and (b) administering to the individual an amount of azidothymidine that is effective to reduce the severity or incidence of symptoms associated therewith.

As will be appreciated, effective dose ranges will generally depend on the route of administration and the patient's sensitivity to the drug. For example, for the preferred route of oral administration, dose ranges of between about 100 and about 4000 mg/day are administered until the symptoms are abated. More preferably, dosages of between about 400 and about 2000 mg azidothymidine/day are administered. Doses of about 800 mg/day have typically been found to be a convenient dose.

For parenteral routes, such as intravenous, intrathecal, intramuscular, etc., administration, typically doses are on the ordr of about ½ the dose employed for oral administration.

The upper dose limit is generally bounded by the appearance of side effects associated with azidothymidine therapy. Such side effects have been found to include primarily hematologic abnormalities such as anemia, neutropenia, bone marrow toxicity, headache, mild CNS symptoms, insomnia, etc. Accordingly, it will be appreciated by those of skill that the onset of any such side effects should be accompanied by a concommital reduction in dosages.

Topical application is achieved through the administration of azidothymidine in a suitable topical dosage form. Generally, a topical dosage form is defined as any dosage form capable of maintaining the azidothymidine in contact with the skin. Such forms include but are not limited to salves, creams, ointments, lotions, pastes, gels, etc. Preferably, to improve the ability of the topical dosage form to maintain the drug in contact with the skin, it is generally desirable to employ a petroleum base topical dosage form that will not be as susceptible to evaporation.

Topical dosage forms are typically formulated to have a concentration of azidothymidine of between about 0.25% and about 10%, and more preferably about 1% to about 5%.

Following treatment of the disease in accordance with the invention, some benefit will be observed generally in about 12–72 hours. Such a benefit may be sufficient in the treatment of milder forms of the disease, for example, where a topical dosage form such as a cream or ointment is applied to a more localized, milder form of the disease. However, for the treatment of more intractable forms which, for example, may include exfoliative processes, it is more generally desirable to administer the drug orally or parenterally for more extended periods. In these cases, it will generally be desirable to administer the drug continually at a selective dosage, or dosage schedule, until symptoms are alleviated. For very severe forms, it may be desirable to administer the drug for several days or even weeks. In any case, those of skill will recognize that such treatment protocols will generally be modified according to the determinations of a skilled attending physician.

DETAILED DESCRIPTION OF THE PREFERRED EMBODIMENTS

Although azidothymidine has been known to be an agent that is useful under certain circumstances in treating or controlling certain forms of acquired immune deficiency (AIDS), it can now be disclosed that this drug is surprisingly efficacious in the treatment of psoriasis. Although all forms of psoriasis may be benefited through administration of the drug in accordance with the present invention, due to its very pronounced antipsoriatic activity, the drug is particularly desirable for use in treating more severe acute or chronic disease. Moreover, the treatment is particularly useful in the treatment of patients in which the use of immunosuppressive agents such as corticosteroids is contraindicated.

Protocols employing azidothymidine for the treatment of psoriasis are generally similar to those recommended by the manufacturer of AZT, Burroughs Wellcome Drug Co., for use in treating selected AIDS patients. In severely affected patients, it will generally be desirable to achieve such as dose level as may be achieved through the administration of dosages on the order of about 800 to about 1500 mg/day. However, doses up to 4000 mg/day may be employed, depending on the appearance of signs of toxicity such as blood diseases like anemia or other signs of bone marrow toxicity in general. Of course, such dosages may have to be adjusted downward. Due to the fact that AZT likely acts by way of an inhibition of DNA synthesis, its use is contraindicated in pregnant patients.

In such cases where the disease is severe and the dosages employed resulting large, the preferred administration route will be a parenteral or enteral route. In that sufficiently high blood levels may be generally obtained through oral administration, this route will typically be the most desirable. However, intravenous administration may be employed where desired, for example, when it is also necessary to provide parenteral feeding. Generally, intravenous or other parenteral doses will be about half that of oral dosages.

In the treatment of less severe forms of psoriasis, it will generally be desirable to administer a lowered dosage in order to minimize the possibility of side effects. Effective oral doses will range from about 100 mg/day or so upward.

Alternatively, for use in treating skin lesions one may apply a topical dosage form containing an effective amount of azidothymidine directly on to the affected skin. Typically, topical dosage forms include formulations such as pharmaceutically acceptable creams, lotions, ointments, salves, pastes, gels, or other preparations as are known in the art for retaining drugs in contact with the affected areas for an extended time. In such dosage forms it is contemplated that concentrations of azidothymidine ranging from about 0.25% to about 10%, and more preferably, about 1% to about 5%, will prove to be the most convenient and effective. In such dosage forms and at such concentrations, the toxicities associated with azidothymidine should be minimal if any.

Under certain circumstances, it will also be desirable to include in topical formulations an agent capable of providing a secondary benefit and/or improve the absorption of drug into the affected skin. Accordingly, in certain embodiments, topical azidothymidine preparations are formulated to include a topical corticosteroid, keratolytic agent, or other cutaneous surface acting anti-psoriatic agent as are generally known in the art. Such agents include, for example, substituted phenols such as cresol, tars such as coal tar, sulfur, icthammol, and anthraline. Numerous other similar agents useful as surface acting anti-psoriatics are well known and are included within the scope of the invention.

Generally, an amount of the secondary agent as is known in the art to be effective in the particular treatment envisioned is included in the topical preparation. Thus, in the case of a corticosteroid such as triamcinolone, a concentration of about 0.03% to about 1% is preferred. Effective concentrations of other corticosteroids and cutaneous surface acting antipsoriatic agents are generally well known in the art and may be determined by reference to the Physician's Desk Reference (PDR) or Goodman et al. (1985), *The Pharmacological Basis of Therapeutics*, 7th Edition.

As with the treatment of severe disease, it will generally be most desirable to continue the treatment until at least some of the symptoms associated with the disease have been abated. Thus, treatment may be indicated for extended periods which, for some patients, may be necessary until the disease has otherwise run its course.

Of the following examples, examples I through IV disclose toxicity data obtained from the manufacturer of AZT, Burroughs Wellcome Drug Co., developed during the course of obtaining FDA approval for use of the drug in the treatment of AIDS. However, treatment protocols effective in treating psoriasis are similar. Thus, this data should be helpful in demonstrating the toxicology and dosaging of azidothymidine to those who may be unfamiliar. Example V demonstrates the successful treatment of an individual suffering from severe psoriasis secondary to acquired immune deficiency syndrome. While the azidothymidine exhibited no efficacy in relieving the progression of this individual's AIDS, the psoriasis began to clear in 24 hours, with significant improvement over a period several weeks.

EXAMPLE I

Animal and In Vitro Toxicity Testing

By the intravenous (IV) route, the LD50 of azidothymidine is greater than 70 mg/kg in rats and mice. No significant alterations were seen when the compound was administered to dogs at intravenous (IV) dose levels up to 85 mg/kg/day IV for 2 weeks. Similarly, no changes were noted in rats given the drug IV, at dose levels up to 150 mg/kg/day IV for one month.

In an oral Dose Range-Finding (DRF) study in rats which were given the compound at dose levels up to 500 mg/kg/day, very minimal histologic changes in the liver and kidney of a few animals were observed.

More notable effects were seen in an oral DFR study in Beagle dogs administered 0, 125, 250, or 500 mg/kg/day at AZT daily for 2 weeks. Vomiting and fecal alterations (with blood) were seen in dogs receiving high doses. Moderate to marked leukopenia and thrombocytopenia was noted at all dose levels. Further studies suggest that these changes result from hypocellularity of the bone marrow; hypoactive lymphoid tissues were also noted. One female dog was sacrificed after significant weight loss on day 14. In that dog, alkaline phosphatase, BUN, and creatinine were elevated, perhaps an effect of dehydration. Grossly, hemorrhage in the gastrointestinal tract in the high dose dogs and a mid-dose female, as well as a maturational defect with mucosal atrophy in the intestinal tract of the high dose female were observed.

In an oral DRF study conducted in Cynomolgus monkeys (a species which metabolizes AZT more like man than the drug disposition pattern seen in dog), dose levels of 125, 250, 500 mg/kg/day of AZT were given for 2 weeks. The only changes seen that may have been treatment-related were frequent vomiting in the high dose male, a slight nondose-related decrease (values still within normal limits) in RBC, HCT, Hgb at all treatment levels, and a slight increase in SGPT (Values still within normal limits) in treated males and the high dose female.

A 13 week oral toxicity study was conducted in Cynomolgus monkeys given 34, 100, or 300 mg/kg by gavage. The results showed dose-related decreases in RBCs, hemoglobin, and hematocrit at day 21. Throughout the remainder of treatment period, hemoglobin and hematocrit remained stable; RBCs, however, were further reduced until the end of treatment. These values returned to normal limits during the 26–39 day post-dosing recovery period.

A 13 week oral toxicity study was conducted in rats given AZT at doses of 56, 167 or 500 mg/kg/day by gavage in distilled water. A control group received water only. Rats were observed for weight changes, food intake, toxicity, opthalmologic changes, hematology and clinical chemistries. There were no treatment related deaths. Clinically, there was occasional staining of the anogenital area in high dose male rats. A mild increase in glucose was observed only in high dose female rats on day 89. In addition, there was a mild decrease in SGOT in high dose rats at various times. There were no hematologic changes or gross pathologic changes.

In an oral DRF study in pregnant rats given AZT at dose levels up to 500 mg/kg from gestation day 6 through 15, a slight decrease in maternal weight was noted.

In genetic toxicology experiments, the AMES test was negative, whereas the drug was a weak mutagen at the highest concentrations tested (1000 to 5000 micrograms/ml) in the mouse lymphoma assay. In an in vitro cytogenetics assay in cultured human lymphocytes, AZT was clastogenic, with the no-effect level being between 3 and 10 micrograms/ml.

EXAMPLE II

Human Pharmacokinetics

Pharmacokinetic data was analyzed for 19 patients receiving intravenous AZT and for 18 of these patients who have also received oral drug. The number of patients at each dose level is shown below:

| Group | Dosing Schedule (n) IV | Oral |
|---|---|---|
| A | 1.0 mg/kg Q 8 hr (4) | 2.0 mg/kg Q 8 hr (3) |
| B | 2.5 mg/kg Q 8 hr (6) | 5.0 mg/kg Q 8 hr (6) |
| C | 2.5 mg/kg Q 4 hr (2) | 5.0 mg/kg Q 4 hr (4) |
| D | 5.0 mg/kg Q 4 hr (4) | 10.0 mg/kg Q 4 hr (2) |
| E | 7.5 mg/kg Q 4 hr (3) | 15.0 mg/kg Q 4 hr (3) |

AZT exhibited a biexponential decay after the end of infusion indicating two-compartmental pharmacokinetics. The mean AZT half-life at all dose levels following IV and oral dosing was approximately 1.0 hr. AZT concentrations increased proportionally with doses to 5.0 and 10 mg/kg, for IV and oral administration respectively, indicating dose-independent kinetics up to these dosages. However, a disproportional increase in peak concentrations (Cmax) and area under the plasma-concentration time curve (AUC) occurred between the 5.0 and 7.5 mg/kg IV and the 10.0 and 15 mg/kg oral dose levels. AZT Cmax levels are shown below:

| Group | Cmax (microgram/ml) IV | Oral |
|---|---|---|
| A | 0.44 ± 0.14 | 0.53 ± 0.11 |
| B | 1.17 ± 0.49 | 1.37 ± 0.58 |
| C | 1.06 ± 0.03 | 1.57 ± 0.81 |
| D | 2.28 ± 0.31 | 3.14 ± 0.73 |
| E | 4.71 ± 0.79 | 10.40 ± 3.47 |

The total body clearance of IV doses from 1.0 to 5.0 mg/kg was approximately 1900 ml/min/70 kg. At 7.5 mg/kg the mean clearance decreases to 1200 mg/min/70 kg. However, the numbers of patients studied were small, and this observation of dose-dependent kinetics at the highest dose level need to be confirmed in more patients.

Renal clearance of AZT was estimated to be about 500 ml/min. The 5'-glucuronide of AZT (GAZT) has been identified as a major plasma and urinary metabolite. The plasma levels of this inactive metabolite were approximately 2-3×the corresponding AZT level. GAZT was rapidly cleared from plasma, with a half-life of about 1 hour. Following IV dosing about 25% of the dose is excreted unchanged in the urine as AZT and about 60% as GAZT.

Following oral administration at all dose levels, the bioavailability was about 60-70%. The incomplete bioavailability appears to be due to first-pass metabolism, rather than reduced absorption. No unexpected drug or metabolite accumulation was observed following chronic IV or oral dosing.

EXAMPLE III

Phase I Study

A Phase I trial to evaluate safey and pharmacokinetics in humans was conducted in 29 patients with AIDS OR AIDS-related complex and HTLV-III/LAV viremia according to the dosage schedules listed in Example II. An initial six-week treatment regimen at the scheduled dosage was followed by a variable observation period. Most patients were then allowed to continue long-term therapy if there had been no serious adverse experiences. Data was available for treatment for at lease 6 months; four patients have been treated for over 1 year (14 months). Headache, the most frequently reported adverse experience, occurred in 8 patients. Three patients experienced mild confusion or anxiety. In one case, this occurred during a febrile episode. A transient erythematous rash occurred in one patient and one other patient reported one episode of generalized pruruitis.

Four deaths have occurred during the year since the trial was initiated. One patient with aggressive gastrointestinal Kaposi's sarcoma at entry had continued progression of the disease. He was removed from the protocol after only 3 weeks in order to receive cytotoxic therapy. Death ensued five months later. One patient died of disseminated cryptococcemia two months after being removed from the study because of anemia. The third patient died of pneumonia after having stopped therapy of his own accord. The fourth patient required successive dose reductions for hematologic toxicity after 4 months of treatment and died of pneumonia at 8 months.

The most common laboratory abnormalities are hematologic. Although all patients had some decline in hemoglobin by six weeks, the change was not proportional to the starting dose. Twenty of 28 patients receiving doses greater than 500 mg orally every 4 hours developed anemia which warranted either a dose reduction or temporary interruption of treatment. Anemia has been reversible in most patients when the drug is discontinued. Bone marrow biopsies performed on three patients revealed megaloblastic changes. One of these patients had pernicious anemia responsive to B12 therapy. Neutropenia occurred in 13 patients and appeared to be the dose-limiting toxicity. Neutropenia responded favorably to reduction in dose of AZT.

Five patients had transient elevations in transaminases. In one patient this correlated with presence of hepatitis B antigen. In another patient, hepatitis was observed during simultaneous administration of pentamidine. There was no effect on electrolytes or renal or cardiac function.

EXAMPLE IV

Phase 2 Study

Two hundred eighty one (281) patients (AIDS) recovered from Pneumocystis carinii pneumonia (PCP) and late AIDS-Related Complex (ARC) were entered over a four month period into a placebo controlled study which was scheduled to last six months. Half of the patients were assigned to receive AZT at a dose of 250 mg every 4 hours (1.5 grams daily) and half to received placebo. Many patients on AZT required a reduction in dosage or interruption of treatment, primarily because of anemia. The groups were comparable at entry for a variety of variables including age, sex, race, weight, mean Karnofsky score, and severity of illness.

As of Sept. 18, 1986 seventeen deaths had occurred: 16 in patients receiving placebo and one in a patient receiving the full dosage of AZT. In general, the deaths were attributed to opportunistic infections, e.g., toxoplasmosis, PCP, CMV, cryptocococcis and mycobacteriosis. Because of the marked imbalance in mortality, primarily in AIDS patients, an independent Data Safety and Monitoring Board (DSMB) reviewed the data (on Sept. 18, 1986) and recommended that the study be terminated. Patients had received between 3½ to 7 months of therapy (median of 4.5 months) at the time the placebo group was discontinued.

A preliminary review of the results prepared for the DSMB indicates that 47 of 145 patients receiving AZT experienced greater than 25% reduction in hemoglobin, compared with 13 of 137 patients receiving placebo. Blood transfusions were required for approximately 25% of the patients receiving AZT and very few of those on placebo. In general, decreases in hemoglobin and neutrophils occurred during the second month of therapy and appeared to be reversible if the dose was decreased or drug discontinued. However, cumulative toxicity manifested as progressive suppression of hematologic parameters may theoretically occur with continued administration of AZT and only a few patients have received the drug for more than 6 months.

EXAMPLE V

Use of Azidothymidine In the Treatment of Severe Psoriasis

A 27 year old individual developed severe psoriasis and AIDS-related complex (ARC). As his immunity diminished over the next eight months to a T4 count of 14/mm³, the psoriasis became more extensive, including 60% of his body, all nails and digits.

Ten months after developing the ARC and psoriasis, the individual developed *Pneumocystis carinii* pneumonia (PCP) and esophageal candidiasis. When the individual was placed on therapy of 800 mg azidothymidine orally per day, a significant improvement in the lesion pruritus was noted within 24 hours. The psoriasis completely cleared over the next two to three weeks. The AZT was held for 7 days after a month for anemia and restarted at half dose. The pruritus returned temporarily. At three months, nail regrowth was normal and the psoriasis was completely clear.

EXAMPLE VI

Preparation of a Topical Dosage Form (Cream)

| Ingredient | Weight (g) |
|---|---|
| Azidothymidine | 5.00 |
| Polawax TM emsulifying wax | 10.00 |
| Cetostearyl alcohol | 6.75 |
| White soft paraffin | 12.50 |
| Liquid paraffin | 5.00 |
| Chlorocresol | 0.10 |
| Purified water | q.s. to 100.00 |

The azidothymidin is dissolved in a mixture of purified water and glycerol and heated to 70° C. The remaining ingredients are heated together at 70° C. The two parts are added together and emsulsified. The mixture is cooled and filled into containers.

EXAMPLE VII

Preparation of a Topical Dosage Form (Ointment)

| Ingredients | Weight (g) |
|---|---|
| Azidothymidine | 5.0 |
| White soft paraffin | 95.0 |

The white soft paraffin is melted at 60° C. The active ingredient is added and dispersed, allowed to cool, and filled into collapsible metal tubes.

What is claimed is:

1. A method for the treatment of psoriasis comprising administering to an individual having psoriasis an amount of azidothymidine that is effective to reduce symptoms of inflammation, irritation, or incidence or size of lesions, associated with this disease.

2. The method of claim 1 wherein azidothymidine is administered orally at a dose range of from about 100 mg/day to about 4000 mg/day until the symptoms are abated.

3. The method of claim 1 wherein azidothymidine is administered orally at a dose range of from about 400 mg/day to about 2000 mg/day until the symptoms are abated.

4. The method of claim 1 wherein azidothymidine is administered orally at a dose of about 800 mg/day until the symptoms are abated.

5. The method of claim 1 wherein azidothymidine is administered parenterally at dose ranges of from about 100 to about 2000 mg/day until the symptoms are abated.

6. The method of claim 1 wherein azidothymidine is administered parenterally at dose ranges of from about 200 to about 1000 mg/day until the symptoms are abated.

7. The method of claim 1 wherein azidothymidine is administered parenterally at a dose of about 400 mg/day until the symptoms are abated.

8. The method of claim 1 wherein the azidothymidine is applied topically to lesions or inflamed tissues in an effective amount until the inflammation, irritation, incidence or severity is abated.

9. The method of claim 8 wherein azidothymidine is applied in a topical dosage form.

10. The method of claim 9 wherein the topical dosage form comprises a pharmaceutically acceptable salve, cream, lotion, ointment, paste or gel having from about 0.25% to about 10% azidothymidine.

11. The method of claim 10 wherein the topical dosage form comprises from about 1% to about 5% azidothymidine.

12. A method for the treatment of psoriasis comprising:
 (a) orally administering to an individual having psoriasis between about 200 and about 4000 mg of azidothymidine per day; and
 (b) continuing the administration until symptoms of psoriasis have been abated.

13. A method for the treatment of psoriasis comprising:
 (a) parenterally administering to an individual diagnosed as having psoriasis between about 100 and about 2000 mg of azidothymidine per day; and
 (b) continuing the administration until symptoms of the disease have abated.

14. A method for treatment of psoriasis comprising:
 (a) topically administering to an area of human skin affected by psoriasis a topical dosage form which includes azidothymidine in a concentration of between about 0.25% and about 10%; and
 (b) continuing the administration until symptoms of psoriasis are abated.

15. The method of claim 14 wherein the topical dosage form includes azidothymidine in a concentration of between about 1% and about 5%.

16. A pharmaceutical composition comprising azidothymidine in a pharmaceutically acceptable topical dosage form selected from a salve, cream, ointment, lotion, paste or gel.

17. The composition of claim 16 wherein the topical dosage form comprises from about 0.25% to about 10% azidothymidine.

18. The composition of claim 17 wherein the topical dosage form comprises from 1% to about 5% azidothymidine.

19. The composition of claim 16 further comprising an effective amount of a corticosteroid.

20. The composition of claim 16 further comprising an effective amount of a cutaneous surface-acting anti-psoriatic agent.

21. The composition of claim 20 wherein the cutaneous surface-acting anti-psoriatic agent is a substituted phenol, tar, sulphur, icthammol, cresol or anthralin.

* * * * *